(12) United States Patent
Collas et al.

(10) Patent No.: US 9,399,781 B2
(45) Date of Patent: Jul. 26, 2016

(54) PRODUCTION OF ISOPROPANOL BY IMPROVED RECOMBINANT STRAINS

(71) Applicants: IFP ENERGIES NOUVELLES, Rueil-Malmaison (FR); STICHTING DIENST LANDBOUWKUNDIG ONDERZOEK, Wageningen (NL)

(72) Inventors: Florent Collas, Wageningen (NL); Remy Marchal, Chatou (FR); Benjamin Clement, Saint Maur des Fosses (FR); Ana Maria Lopez Contreras, Utrecht (NL); Pieternel A.M Claassen, Wageningen (NL)

(73) Assignees: IFP ENERGIES NOUVELLES, Rueil-Malmaison (FR); STICHTING DIENST LANDBOUWKUNDIG ONDERZOEK, Wageningen (NL)

( * ) Notice: Subject to any disclaimer, the term of this patent is extended or adjusted under 35 U.S.C. 154(b) by 0 days.

(21) Appl. No.: 14/350,923

(22) PCT Filed: Oct. 3, 2012

(86) PCT No.: PCT/FR2012/052239
§ 371 (c)(1),
(2) Date: Apr. 10, 2014

(87) PCT Pub. No.: WO2013/054022
PCT Pub. Date: Apr. 18, 2013

(65) Prior Publication Data
US 2014/0322778 A1    Oct. 30, 2014

(30) Foreign Application Priority Data
Oct. 11, 2011 (FR) .................................. 11 59175

(51) Int. Cl.
| | |
|---|---|
| C12P 7/04 | (2006.01) |
| C12N 9/00 | (2006.01) |
| C12N 9/10 | (2006.01) |
| C12N 9/04 | (2006.01) |
| C12N 9/88 | (2006.01) |
| C12N 15/52 | (2006.01) |
| C12P 7/06 | (2006.01) |
| C12P 7/16 | (2006.01) |
| C12P 7/18 | (2006.01) |
| C12P 7/52 | (2006.01) |
| C12P 7/54 | (2006.01) |

(52) U.S. Cl.
CPC .................. *C12P 7/04* (2013.01); *C12N 9/0006* (2013.01); *C12N 9/1029* (2013.01); *C12N 9/13* (2013.01); *C12N 9/88* (2013.01); *C12N 15/52* (2013.01); *C12P 7/065* (2013.01); *C12P 7/16* (2013.01); *C12P 7/18* (2013.01); *C12P 7/52* (2013.01); *C12P 7/54* (2013.01); *Y02E 50/10* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 2008/0293125 A1* | 11/2008 | Subbian | ...................... | C12P 7/04 435/252.3 |
| 2010/0203604 A1* | 8/2010 | Yukawa | ............... | C12N 9/0006 435/157 |

FOREIGN PATENT DOCUMENTS

| | | |
|---|---|---|
| EP | 2 182 051 A1 | 5/2010 |
| WO | 2008/131286 A1 | 10/2008 |
| WO | 2009/103026 A1 | 8/2009 |

OTHER PUBLICATIONS

Hanai T et al.: "Engineered synthetic pathway for isopropanol production in *Escherichia coli*", Applied and Environmental Microbiology Dec. 2007 American Society for Microbiology US, vol. 73. No. 24, Dec. 2007, pp. 7814-7818, XP002671906.001: DOI:10.1128/AEM.01140-07 abrege p. 7814 colonne de gauche, ligne 23—colonne de droite. ligne 21 figure 1 p. 7817, colonne de droite ligne 7—ligne 22, French Search Report and ISR.

Toru Jojima et al.: "Production of isopropanol by metabolically engineered *Escherichia coli*", Applied Microbiology and Biotechnology, Springer. Berlin. DE, vol. 77. No. 6. Nov. 7, 2007. pp. 1219-1224. XP019586231, ISSN: 1432-0614, DOI: 10. 1007/S00253-087-1246-8 [extrait le 2887-11-07], abrege p. 1219. colonne de droite. ligne 27—p. 1228. colonne de gauche, ligne 3, p. 1222. colonne de droite, ligne 11—ligne 16, p. 1223. colonne de droite, ligne 2—1 i gne 13, French Search Report and ISR.

French Search Report, dated Mar. 21, 2012, from corresponding FR application.

International Search Report, dated Dec. 18, 2012, from corresponding PCT application.

\* cited by examiner

*Primary Examiner* — Suzanne M Noakes
(74) *Attorney, Agent, or Firm* — Young & Thompson

(57) ABSTRACT

The expression vector includes: the nucleic acids coding for the polypeptides forming a polypeptide complex having an enzyme activity allowing acetoacetyl-CoA to be converted to acetoacetate; optionally, at least one nucleic acid coding for a polypeptide having an enzyme activity allowing acetoacetate to be converted to acetone; and at least one nucleic acid coding for a polypeptide having an enzyme activity allowing acetone to be converted to isopropanol; the expression of the nucleic acids being controlled by a single constitutive promoter located upstream of the abovementioned nucleic acids.

10 Claims, 3 Drawing Sheets

PRODUCTION OF ISOPROPANOL BY IMPROVED RECOMBINANT STRAINS

Figure 1:
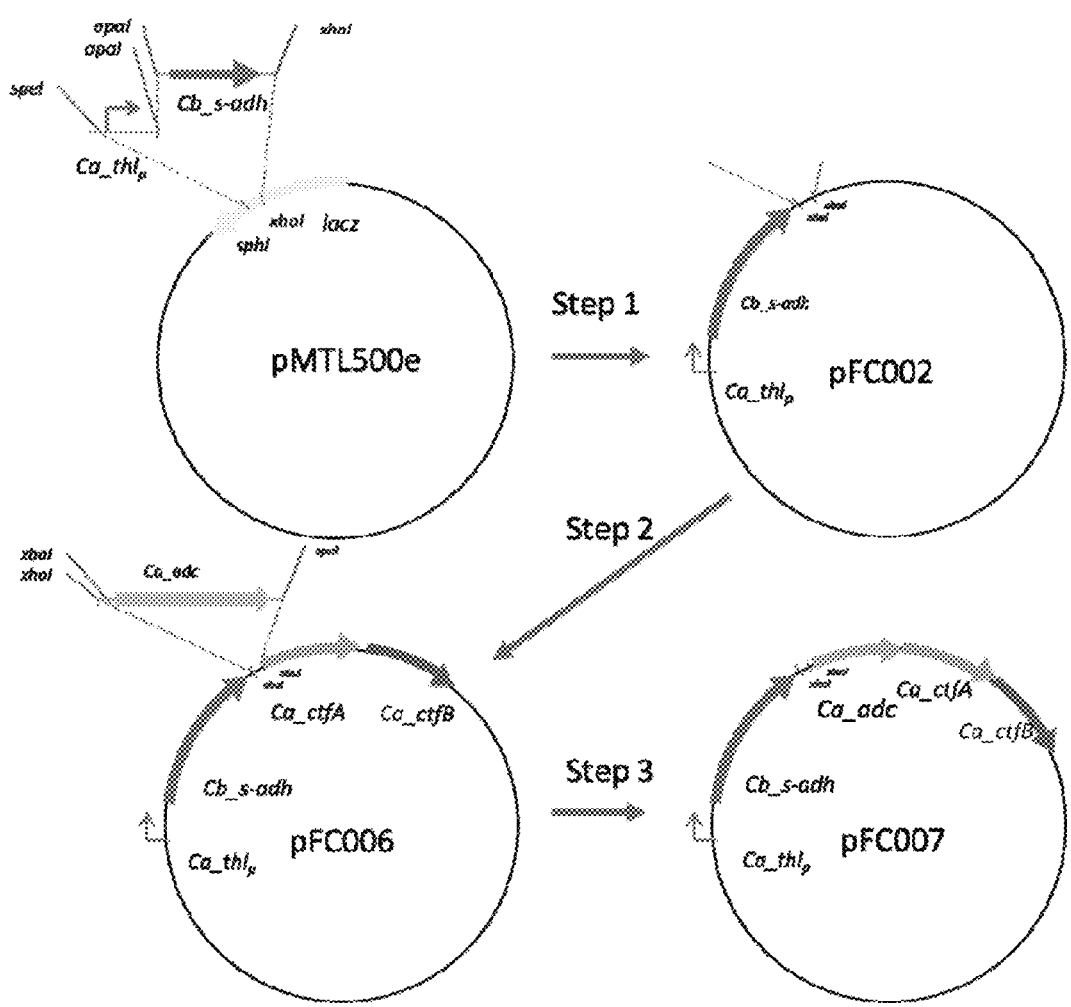

The present invention relates to a method for the production of isopropanol by improved recombinant strains.

BIBLIOGRAPHICAL RESEARCH

Isopropanol, also called 2-propanol, or isopropyl alcohol, is mainly used as a solvent for preparing inks and surfactants. Its other applications relate to the antiseptic and solvent properties of carboxymethylcellulose (CMC). Isopropanol is also used in the production of bases for cosmetics, as a solvent for pesticides or as a source of material in organic synthesis. As an indication, it may be mentioned that the production of isopropanol reached 45 million tonnes in the USA in 1990 (Papa A, 2005).

Nowadays, isopropanol is produced by an essentially chemical method consisting of hydration of propylene by a direct or indirect route. The indirect route uses two steps. In the first step, a mixture of mono- and di-isopropyl sulphuric esters is produced, which is hydrolysed to isopropanol in a second step. The direct route uses the hydration of propylene at high pressure and low temperature on a "fixed-bed" acid catalyst (Logsdon J. E. and Loke R. A., 2001).

From 1942 to 1958, isopropanol was produced in Taiwan by fermentation (Rogers et al. 2006). The substrates for the fermentation were sweet potato, cassava, and wheat starch, whereas the microorganism was a wild-type strain. Nowadays, this method for the production of isopropanol is no longer used industrially. In fact, the low yields obtained with wild-type strains (between 2 and 3 g/L of isopropanol for *Clostridium beijerinckii*) do not allow economically viable processes to be developed. Just like ABE (Acetone, Butanol, Ethanol) solventogenic fermentation, IBE (Isopropanol, Butanol, Ethanol) fermentation was abandoned at the beginning of the 1960s in parallel with the development of the petrochemical industry.

For ecological and economic reasons, research into the production of isopropanol by microbiological fermentation has experienced renewed interest in recent years. Isopropanol-producing fermentation is known as IBE fermentation. It differs from another solvent-producing fermentation, ABE fermentation, in that it produces isopropanol, solely or primarily, at the expense of acetone. The solvent-producing strains belong to the genus *Clostridium*. They have been reclassified into four species: *C. acetobutylicum*, *C. beijerinckii*, *C. aurantibutyricum*, *C. saccharoperbutylacetonicum* (Keis et al. 2001).

*C. acetobutylicum* is a strain that is often used in ABE fermentation. The main products from fermentation with *C. acetobutylicum* are therefore acetone, ethanol and butanol. Isopropanol is not produced by the wild-type strains of *C. acetobutylicum*. Isopropanol is a product that is characteristic of a microorganism formerly called "*Clostridium butylicum*" (Osburn et al. 1937; Langlykke et al. 1937). In 1983, George et al. showed that *C. butylicum* is similar to *C. beijerinckii*. In the current classification, the species *C. beijerinckii* therefore contains strains that were formerly classified as *C. butylicum*. However, not all strains of *C. beijerinckii* produce isopropanol. For example, the strain *C. beijerinckii* NRRL B593 does produce it, whereas the strain *C. beijerinckii* NRRL B592 does not.

The biosynthetic pathway of isopropanol in *C. beijerinckii* comprises the following steps:
(i) two molecules of acetyl-CoA are condensed to one molecule of acetoacetyl-CoA by acetyl-CoA transferase (EC 2.3.1.9), also called thiolase (Thl);
(ii) the CoA of acetylCoA is transferred to the acetate or to the butyrate by acetoacetyl-CoA transferase (Ca_CtfAB) (EC 2.8.3.9) to give the acetoacetate;
(iii) the acetoacetate is then converted to acetone and $CO_2$ by acetate decarboxylase (Ca_Adc) (EC 4.1.1.4);
(iv) finally, the acetone is converted to isopropanol by secondary alcohol dehydrogenase (Cb_s-Adh) (EC 1.1.1.2).

Comparison of the enzyme activities in *C. beijerinckii* NRRL B593 and *C. beijerinckii* NRRL B592 (which produce and do not produce isopropanol, respectively) showed that the capacity for isopropanol excretion was linked to the activity of secondary alcohol dehydrogenase Cb_s-Adh (Yan et al. 1988). The enzyme responsible was purified from acellular extracts of *C. beijerinckii* NRRL B593 (Ismaiel et al. 1993). The dehydrogenase of *C. beijerinckii* NEST255 was also purified for purposes of comparison. The secondary alcohol dehydrogenases in the strains *C. beijerinckii* NRRL B593 and *C. beijerinckii* NEST255 are NADP-dependent. In vitro, they utilize secondary alcohols (isopropanol) as expected, but also primary alcohols, in particular butanol, but with lower activity. Kinetic studies of the enzyme confirmed that the physiological substrate of the secondary alcohol dehydrogenase was indeed acetone and not isopropanol (Chen et al. 1995). The secondary alcohol dehydrogenase in *C. beijerinckii* (Cb_s-Adh) is clearly distinct from the primary alcohol dehydrogenase originating from the same microorganism, which in vivo reduces butyraldehyde to butanol.

The gene coding for Cb_s-Adh has been sequenced (Petretz et al. 1997). The structure of the enzyme was determined by X-ray analysis. Cb_s-Adh is a homotetrameric zinc enzyme having four polypeptide chains of 351 amino acids. Each monomer is constituted by two domains. The first domain (residues 154-294) allows binding of the cofactor whereas the second domain incorporates the catalytic domain (residues 1-153 and 295-351) (Korkhin et al. 1998; Goihberg et al. 2010). Cb_s-Adh is similar to its homologue originating from the thermophilic bacterium *Thermoanaeobacter brockii* (Tb_s-Adh) with 75% sequence identity. In terms of properties, the two enzymes differ in their thermal stability (Korkhin et al. 1999). Replacement, in Cb_s-Adh, of Gln100 with Pro100 in the amino acid sequence significantly increases the thermal stability of Cb_s-Adh (Goihberg et al. 2007), which is originally lower.

The maximum capacity for producing isopropanol is relatively low (2 to 3 g/L) with the wild-type strains of *C. beijerinckii* (Chen et al., 1986). Patent application US2009/246842 describes a method for the production of isopropanol in a strain of *E. coli* transformed by an expression vector comprising the gene coding for acetyl-CoA transferase of *C. acetobutylicum* (Ca_thl), the genes coding for acetoacetyl-CoA transferase of *C. acetobutylicum* (Ca_CtfAB), the gene coding for an acetate decarboxylase (Ca_adc) of *C. acetobutylicum* and the gene coding for the secondary alcohol dehydrogenase (Cb_s-adh) of *C. beijerinckii*. In this vector, expression of the secondary alcohol dehydrogenase is under the control of the promoter $P_{LlacO-1}$ which can be induced by IPTG, whereas expressions of the genes Ca_thl, Ca_CtfAB and Ca_adc are under the control of the native promoter of the Ca_thl gene of *C. acetobutylicum*. The drawback of this method is that it is necessary to use a rich production medium, in particular yeast extract (5 g·$L^{-1}$), and an inducer, such as isopropyl-β-thiogalactopyranoside or IPTG. Moreover, the secondary alcohol dehydrogenase is expressed only when IPTG is added to the culture medium, which delays the production of isopropanol and limits the fermentation productivity.

International application WO 11/037414 describes another method capable of producing isopropanol. This method consists of using microorganisms of the genus *Clostridium* transformed by an expression vector comprising the gene coding for the acetate decarboxylase (Ca_adc) of *C. acetobutylicum*, the genes coding for the acetoacetyl-CoA transferase of *C. acetobutylicum* (Ca_CtfAB) and the gene coding for the secondary alcohol dehydrogenase (Cb_s-adh) of *C. beijerinckii*. This vector requires two promoters: a constitutive promoter Ca_thl$_p$ which only controls the expression of the secondary alcohol dehydrogenase and an inducible promoter Ca_adc$_p$ which controls the expression of the proteins Ca_CtfAB and Ca_Adc. Given that the proteins Ca_CtfAB and Ca_Adc are expressed only during the solventogenesis phase, the secondary alcohol dehydrogenase does not have a substrate (acetone) before this phase. As a result, isopropanol, the end product of fermentation, is produced only after 15 hours of culture, which limits the isopropanol productivity of this method of production.

Consequently, there is still a need to develop a method for the production of isopropanol with a better productivity and a better yield.

The objective of the present invention is to rectify the drawbacks of the prior art and to propose a method for the production of isopropanol by fermentation having a better productivity and a better yield.

DESCRIPTION OF THE INVENTION

The inventors have discovered that it is possible, advantageously, to produce isopropanol using recombinant microorganisms into which vectors have been introduced comprising the genes coding for the enzymes of the metabolic pathway leading from acetoacetyl-CoA to acetone, namely CoA transferase subunits A and B and acetoacetate decarboxylase, as well as the gene coding for a secondary alcohol dehydrogenase of *C. beijerinckii* NRRL B593.

The first objective of the present invention is to provide an expression vector comprising:
the nucleic acids coding for the polypeptides forming a polypeptide complex having an enzyme activity allowing acetoacetyl-CoA to be converted to acetoacetate,
at least one nucleic acid coding for a polypeptide having an enzyme activity allowing acetone to be converted to isopropanol, and
optionally, at least one nucleic acid coding for a polypeptide having an enzyme activity allowing acetoacetate to be converted to acetone,
the expression of said nucleic acids being controlled by a single constitutive promoter located upstream of the above-mentioned nucleic acids.

By "expression vector" is meant an exogenous DNA molecule of circular shape, which is capable of autonomous and independent replication of the chromosomal DNA of the host cells, allowing transcription and translation of the genes contained in said DNA molecule by means of the host cells.

In the present invention, the term "vector" and the term "plasmid" are interchangeable.

By "promoter" is meant a region of DNA where RNA polymerase binds and orients this enzyme towards the site where transcription of the gene will begin.

The promoters can be constitutive or inducible.

By "constitutive promoter" is meant an unregulated promoter allowing continuous transcription of the associated gene.

In contrast to a constitutive promoter, an inducible promoter allows transcription of the associated gene in response to the presence of a particular compound, for example the presence of IPTG, or to a defined external condition, for example a high temperature.

By "a promoter . . . located upstream of the . . . nucleic acids" is meant a promoter located before the 5' ends of the nucleic acids.

The conversion of acetoacetyl-CoA to acetoacetate is carried out by acetoacetyl-CoA transferase. In most microorganisms, this enzyme is formed by two subunits encoded by two different genes. Thus, the acetoacetyl-CoA transferase of *E. coli* (Ato AD) is formed by the units A and D, and the acetoacetyl-CoA transferase of *C. acetobutylicum* (Ca_CtfAB) is formed by the units A and B.

In a particular embodiment, the present invention relates to a vector comprising:
the nucleic acids coding for acetoacetyl-CoA transferase (Ca_CtfAB), and
at least one nucleic acid coding for the gene of the secondary alcohol dehydrogenase of *C. beijerinckii* (Cb_s-adh); and
optionally at least one nucleic acid coding for the gene of acetoacetate decarboxylase (Ca_adc).

Expression of the gene of the secondary alcohol dehydrogenase of *C. beijerinckii* NRRL B 593 makes it possible to ensure conversion of acetone to isopropanol and excretion of the latter. A recombinant strain expressing this enzyme can reduce almost all of the acetone and acetoin (3-hydroxy-2-butanone) to isopropanol and 2,3-butanediol respectively. Although it is known that the enzyme Cb_s-Adh, from the strain *C. beijerinckii* NRRL B 593, can reduce acetone and butanone, the activity of this enzyme on acetoin has been found for the first time by the inventors.

In a more particular embodiment, the present invention relates to a vector comprising:
a nucleic acid represented by the sequence SEQ ID NO: 1, or a nucleic acid having a sequence identity of at least 85%, particularly 90%, in particular 95% with the sequence SEQ ID NO: 1, and
a nucleic acid represented by the sequence SEQ ID NO: 2 or a nucleic acid having a sequence identity of at least 85%, particularly 90%, in particular 95% with the sequence SEQ ID NO: 2, and
a nucleic acid represented by the sequence SEQ ID NO: 3 or a nucleic acid having a sequence identity of at least 85%, particularly 90%, in particular 95% with the sequence SEQ ID NO: 3, and
optionally a nucleic acid represented by the sequence SEQ ID NO: 4 or a nucleic acid having a sequence identity of at least 85%, particularly 90%, in particular 95% with the sequence SEQ ID NO: 4.

The nucleic acid represented by the sequence SEQ ID NO: 1 codes for subunit A of the acetoacetyl-CoA transferase of *C. acetobutylicum* ATCC 824 (Ca_ctfA).

The nucleic acid represented by the sequence SEQ ID NO: 2 codes for subunit B of the acetoacetyl-CoA transferase of *C. acetobutylicum* ATCC 824 (Ca_ctfB).

The nucleic acid represented by the sequence SEQ ID NO: 3 codes for the secondary alcohol dehydrogenase of *C. beijerinckii* (Cb_s-adh).

The nucleic acid represented by the sequence SEQ ID NO: 4 codes for the acetoacetate decarboxylase of *C. acetobutylicum* (Ca_adc).

The percentage identity between two peptide sequences or between two nucleic acid sequences can be calculated from the following formula:

$$\frac{\text{number of identical residues} \times 100}{\text{number of residues of the shorter sequence}}$$

The combinations of the abovementioned nucleic acids (or genes) form the "ipa" operons. Expression of the genes of the abovementioned ipa operons is controlled by a single constitutive promoter located upstream of the abovementioned nucleic acids (or genes). A constitutive promoter, which only controls the expression of the ipa operons, allows constitutive expression of the latter, which allows a recombinant strain containing one of the vectors of the invention to produce isopropanol as from the first hours of fermentation.

Owing to the early expression of the genes that lead to the production of isopropanol, the mechanism of solventogenesis is triggered earlier in a recombinant strain containing a vector according to the invention than in a wild-type strain. Consequently, two fermentation phases, namely, acidogenesis and solventogenesis, take place at the same time in a recombinant strain containing a vector according to the invention, which makes it possible to reduce the fermentation time by at least 20 hours.

The constitutive promoter used in the construction of the vector of the present invention can be the promoter of the gene coding for the thiolase of *C. acetobutylicum* ATCC 824, represented by the sequence SEQ ID NO: 5, or the promoter of the gene of the phosphotransbutyrylase of *C. acetobutylicum* ATCC 824, represented by the sequence SEQ ID NO: 6.

In a particular embodiment, the expression vector of the present invention comprising:
  a nucleic acid represented by the sequence SEQ ID NO: 1, or a nucleic acid having a sequence identity of at least 85%, particularly 90%, in particular 95% with the sequence SEQ ID NO: 1, coding for subunit A of the acetoacetyl-CoA transferase of *C. acetobutylicum* and
  a nucleic acid represented by the sequence SEQ ID NO: 2 or a nucleic acid having a sequence identity of at least 85%, particularly 90%, in particular 95% with the sequence SEQ ID NO: 2, coding for subunit B of the acetoacetyl-CoA transferase of *C. acetobutylicum*, and
  optionally a nucleic acid represented by the sequence SEQ ID NO: 4 or a nucleic acid having a sequence identity of at least 85%, particularly 90%, in particular 95% with the sequence SEQ ID NO: 4, coding for the acetoacetate decarboxylase of *C. acetobutylicum*, and
  a nucleic acid represented by the sequence SEQ ID NO: 3 or a nucleic acid having a sequence identity of at least 85%, particularly 90%, in particular 95% with the sequence SEQ ID NO: 3, coding for the secondary alcohol dehydrogenase of *C. beijerinckii*, the expression of said nucleic acids being controlled by a single constitutive promoter located upstream of the abovementioned nucleic acids, said promoter being selected from the promoter represented by the sequence SEQ ID NO: 5 (thl promoter) and the promoter represented by the sequence SEQ ID NO: 6.

In a particular embodiment, the vector of the present invention comprises:
  a nucleic acid represented by the sequence SEQ ID NO: 1,
  a nucleic acid represented by the sequence SEQ ID NO: 2,
  a nucleic acid represented by the sequence SEQ ID NO: 3,
  a nucleic acid represented by the sequence SEQ ID NO: 4, and
  a promoter represented by the sequence SEQ ID NO: 5.

This vector designated pFC007 contains, in the order from the 5' end to the 3' end, the gene coding for the secondary alcohol dehydrogenase (Cb_s-adh) of *C. beijerinckii* NRRL B 593 as well as the gene coding for the acetoacetate decarboxylase (Ca_adc) and the genes coding for subunits A and B of the coenzyme A transferase (Ca_CtfAB) of *C. acetobutylicum* ATCC 824. The vector pFC007 allows overexpression of the genes of the "ipa7" operon under the control of just one constitutive promoter, that of the gene of the acetyl-CoA transferase (thiolase, Ca_thl) of *C. acetobutylicum* ATCC 824. Consequently, production of their respective enzymes (Cb_s-Adh, Ca_Adc and Ca_CtfAB) begins as from the first hours of fermentation (after approximately 4 and 10 hours).

In another particular embodiment, the vector of the present invention comprises:
  a nucleic acid represented by the sequence SEQ ID NO: 1,
  a nucleic acid represented by the sequence SEQ ID NO: 2,
  a nucleic acid represented by the sequence SEQ ID NO: 3, and
  a promoter represented by the sequence SEQ ID NO: 5.

This vector designated pFC006 contains the gene coding for the secondary alcohol dehydrogenase (Cb_s-adh) of *C. beijerinckii* NRRL B 593 (DSMZ 6423) as well as the genes coding for subunits A and B of the coenzyme A transferase (Ca_CtfAB) of *C. acetobutylicum* ATCC 824. These genes are under the control of just one constitutive promoter of the gene of the acetyl-CoA transferase (or thiolase or Ca_thl) of *C. acetobutylicum* ATCC 824.

The expression vectors according to the present invention can further comprise any other element necessary for the transcription and translation of the aforementioned enzymes, such as an RBS (ribosome binding site) region, one or more selection genes.

An RBS region allows binding of the ribosome to the messenger RNA molecule before the start codon of a gene. The sequence of RBS region used in the vectors of the present invention can be any sequence of RBS region of prokaryotic origin known to a person skilled in the art.

The presence of a selection gene in a vector according to the invention makes it possible to select the microorganisms that have been transformed successfully. A selection gene in a vector allows the microorganisms comprising said gene to survive under certain particular conditions, or can lead to the presence of a molecule that can be easily identified. The selection gene used in the vectors of the present invention can be any selection genes known to a person skilled in the art, in particular a gene endowing the microorganisms with antibiotic resistance, such as the gene Amp, or ErmB.

The expression vectors also comprise replication origins, which allow initiation of the replication of said vectors in the host microorganisms. The replication origin used in the vectors of the present invention can be any replication origin known to a person skilled in the art.

The present invention also aims to provide a recombinant microorganism for producing isopropanol with a better productivity and a better yield.

Said microorganism comprises an expression vector as described in the present invention.

In particular, said microorganism comprises a vector comprising:
  a nucleic acid represented by the sequence SEQ ID NO: 1, or a nucleic acid having a sequence identity of at least 85%, particularly 90%, in particular 95% with the sequence SEQ ID NO: 1, and a nucleic acid represented by the sequence SEQ ID NO: 2 or a nucleic acid having a sequence identity of at least 85%, particularly 90%, in particular 95% with the sequence SEQ ID NO: 2, and a nucleic acid represented by the sequence SEQ ID NO: 3 or a nucleic acid having a sequence identity of at least 85%, particularly 90%, in particular 95% with the sequence SEQ ID NO: 3, and optionally a nucleic acid represented by the sequence SEQ ID NO: 4 or a nucleic acid having a sequence identity of at least 85%, particularly 90%, in particular 95% with the sequence SEQ ID NO: 4, the expression of said nucleic acids being controlled by a single constitutive promoter located upstream of the above-mentioned nucleic acids, said promoter being selected from the promoter represented by the sequence SEQ ID NO: 5 (thl promoter) and the promoter represented by the sequence SEQ ID NO: 6.

In an advantageous embodiment, said microorganism comprises the vector pFC007.

In another advantageous embodiment, said microorganism comprises the vector pFC006.

Said microorganism of the present invention can be selected from bacteria of the genus *Clostridium*, such as *C. acetobutylicum, C. beijerinckii, C. saccharoperbutylacetonicum, C. saccharobutylicum*, bacteria of the genus *Bacillus*, such as *Bacillus subtilis*, or enterobacteria, such as *E. coli*.

In a particular embodiment, the microorganism according to the invention is *C. acetobutylicum*.

In a more particular embodiment, the microorganism according to the invention is the strain *C. acetobutylicum* ATCC 824.

In a particularly advantageous embodiment, the invention relates to a recombinant strain of *C. acetobutylicum* ATCC 824 comprising the vector pFC007. The recombinant strain is designated ATCC 824(pFC007).

In another particularly advantageous embodiment, the invention relates to a recombinant strain of *C. acetobutylicum* ATCC 824 comprising the vector pFC006. The recombinant strain is designated ATCC 824(pFC006).

For the two recombinant strains (ATCC 824(pFC007) and ATCC 824(pFC006)), production of isopropanol can be detected as from the first 10 hours of culture, whereas no trace of solvents (ABE) is detectable in the wild-type strain of *C. acetobutylicum* ATCC 824 or the recombinant strain of *C. acetobutylicum* ATCC 824 into which a vector is inserted that only comprises the gene coding for the secondary alcohol dehydrogenase (Cb_s-adh) of *C. beijerinckii* NRRL B 593.

Another aim of the present invention is to provide a method for the production of isopropanol, and/or of D and L 2,3-butanediol, with a better productivity and a better yield.

Said method comprises at least the following steps:

cultivating a microorganism according to the invention in a culture medium comprising at least one carbon source and one nitrogen source, under conditions allowing the production of isopropanol, for example the culture medium described by Gapes et al. (Gapes, 1996)

recovering the isopropanol, and/or D and L 2,3-butanediol, from the culture medium.

The culture media are known to a person skilled in the art.

The carbon source can be starch, glucose, xylose, lignocellulosic hydrolysates.

The nitrogen source can be ammonia, yeast extract, peptone, urea.

The culture conditions for microorganisms of the genus *Clostridium*, *Bacillus* or the *E. coli* bacteria are known to a person skilled in the art.

The recovery of the isopropanol, and/or D and L 2,3-butanediol, from the culture medium is performed by distillation (Mujiburohman et al. 2006).

The examples and figures presented below illustrate the present invention in more detail. However, the scope of the present invention must in no case be limited to these examples or figures.

FIGURES

FIG. 1: this figure illustrates construction of the vector pFC007 from the plasmid pMTL500E.

Figure 2:
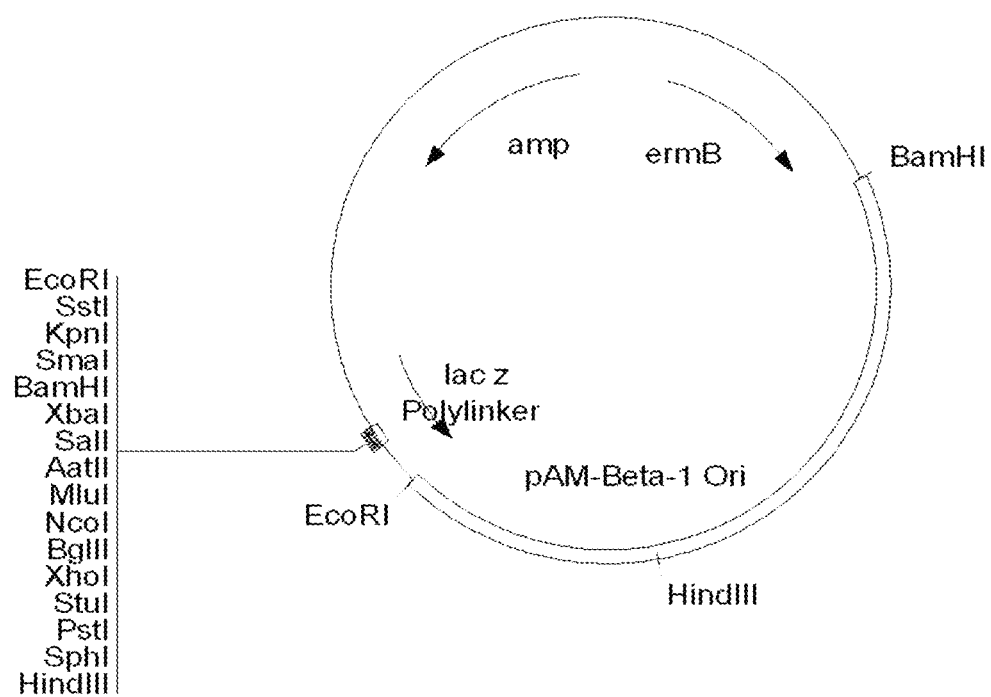

FIG. 2: this figure gives the restriction sites of the plasmid pMTL500E.

Figure 3:
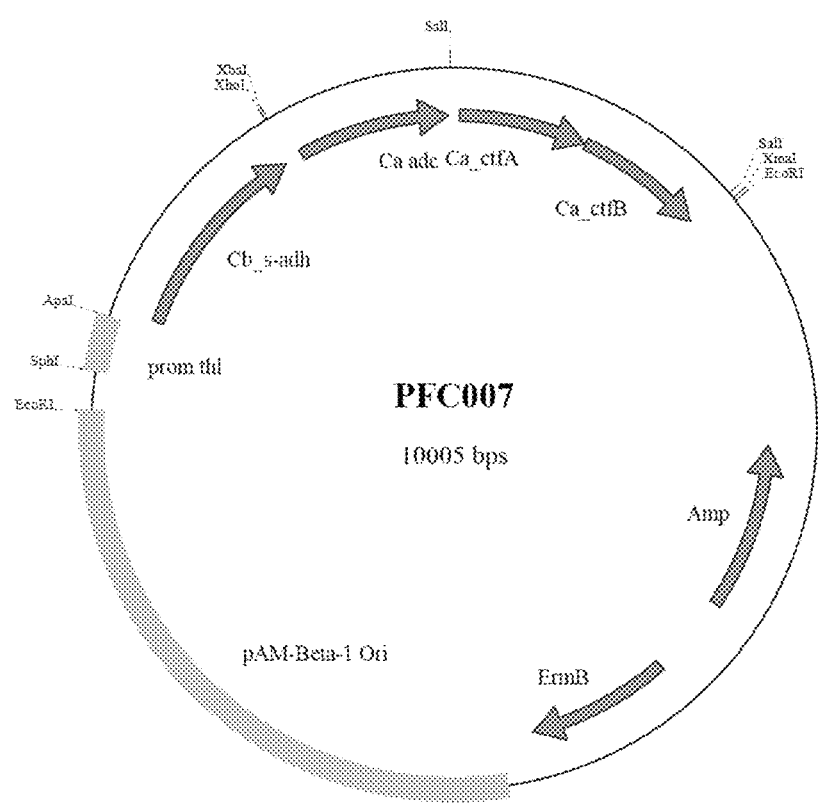

FIG. 3: this figure illustrates the restriction map of the vector pFC007.

EXAMPLES

Materials and Methods
Equipment and Materials

The kits used in the operations of molecular biology (construction of the plasmid vectors) are presented in Table 1.

TABLE 1

Kits and materials used in the operations of molecular biology

| Name of the kit | Use | Supplier |
| --- | --- | --- |
| Restriction enzymes: apaI, speI, sphI, xbaI and xhoI | Enzymatic digestion of plasmid DNAs | New England Biolabs (NEB) |
| High Fidelity PCR Master Mix ™ | PCR amplification | Roche |
| DreamTaq ™ | PCR amplification | Fermentas |
| Oligonucleotides (Table 3) | Primers for the PCR reactions, created by the inventors | BaseClear |
| Alkaline phosphatase | dephosphorylation of the 5' ends of the linearized vectors preventing self-ligation | New England Biolabs |
| T4 DNA ligase | ligation of DNA fragment | New England Biolabs (NEB) |
| GenJET ™ plasmid miniprep | Extraction of plasmid DNA from cultures of *E. coli* | Fermentas |
| GenElute ™ Bacterial Genomic DNA | Extraction of genomic DNA from bacteria (Gram-positive and Gram-negative) | Sigma-Aldrich |
| Z-Competent ™ *E. coli* transformation | Production of chemocompetent bacteria *E. coli* XL1 blue and *E. coli* BW25113 | Zymo Research |

The strains used in the examples of the present invention are:
- C. acetobutylicum ATCC 824, originating from the ATCC collection
- C. beijerinckii NRRL B 593, originating from the DSMZ collection (number 6423)
- E. coli XL1 blue, used for plasmid cloning and maintenance
- E. coli DH10B (PAN2), used for methylation of the plasmids Assaying of Solvents (Acetone, Acetoin, Isopropanol, Butanol, Butanediol) and Carboxylic Acids (Butyric and Acetic Acids)

The fermentation samples (2 mL) are centrifuged for 5 minutes at 20,000 g and the supernatants are used for assaying the fermentation metabolites (glucose, acetic and butyric acid, 2,3-butanediol, acetone, ethanol, isopropanol and butanol). For each sample, an equivolume of an acid solution (0.5 mM $H_2SO_4$) containing the internal standard (30 mM of 4-methylvaleric acid) is added, the mixture is then homogenized and filtered (0.2 µm, Whatman). 10 µL of sample is then injected and analyzed in a Shodex Ionpack KC-811 column (RP). The assayed compounds are detected at column outlet by two detectors: a refractometer (Waters 2487) and a spectrophotometer (Waters 2487) measuring the absorbance at 210 nm. The eluent used is a 3 mM solution of sulphuric acid, the flow rate of the eluent is 1 mL/min and the column temperature is fixed at 85° C.

Construction of the Vectors

The genetic structures of the vectors used or constructed in the examples of the present invention are summarized in Table 2 below.

TABLE 2

Genetic structures of the vectors

| Plasmid | Clostridium/ E. coli selective marker | Description | Reference |
|---|---|---|---|
| pMTL500E | ermB/amp$^R$ | Empty vector | Oultram et al., 1988 |
| pFC002 | ermB/amp$^R$ | Ca_thl$_p$ [Cb_s-adh] | This document |
| pFC005 | ermB/amp$^R$ | Ca_thl$_p$ [Cb_s-adh; Ca_adc] | This document |
| pFC006 | ermB/amp$^R$ | Ca_thl$_p$ [Cb_s-adh; Ca_ctfAB] | This document |
| pFC007 | ermB/amp$^R$ | Ca_thl$_p$ [Cb_s-adh; Ca_adc; Ca_ctfAB] | This document |
| pAN2 | ttc | | (Mermelstein, 1993; Heap, 2009) | ermB: erythromycin resistance gene;
amp$^R$: ampicillin resistance gene;
ttc: tetracycline resistance gene;
Ca: this prefix indicates that the gene originates from C. acetobutylicum ATCC 824;
Cb: this prefix indicates that the gene originates from C. beijerinckii NRRL B593;
Ca_thl: thiolase gene;
Cb_s-adh: gene of the secondary dehydrogenase of C. beijerinckii NRRL B593;
Ca_adc: gene of the acetate decarboxylase of C. acetobutylicum ATCC 824;
Ca_CtfAB: gene of the CoA transferase of C. acetobutylicum ATCC 824.

Construction of the vector pFC007 from the plasmid pMTL500E (FIG. 2) requires at least 3 steps (FIG. 1).

Step 1: Construction of the Vector pFC002

The vector pFC002 is constructed from the plasmid pMTL500E. The latter is digested with the restriction enzymes sphI and xhoI on the lacZ gene. The digestion product is then dephosphorylated. The restriction sites sphI and apaI are added respectively at 5' and 3' of the DNA sequence of the promoter Pthl, by the PCR technique using the primers Ca_thlp-for and Ca_thlp_rev derived from the genomic DNA of C. acetobutyliccum ATCC 824 (Nolling, J. et al., 2001) (NCBI reference: NC_003030.1 (http://www.ncbi.nlm.nih.gov/nuccore/NC_003030) (Table 3). The restriction sites apaI and xhoI are added at 5' and 3' respectively of the DNA sequence of the gene Cb_s-adh of C. beijerinckii NRRL B593, by the PCR technique using the primers Cb_s-adh-for and Cb_s-adh-rev (Table 3).

The PCR product thus obtained is digested with the restriction enzymes apaI and xhoI. The digested plasmid, the digested promoter and the digested gene originating from the PCR are ligated together to give a vector called pFC002 (FIG. 2). This vector is maintained and multiplied in the E. coli strain XL1 blue.

Step 2: Construction of the Vector pFC006 from the Plasmid pFC002

The vector pFC002 is digested with the restriction enzymes xhoI and XbaI. The genes coding for Ca_CtfAB are amplified together starting from the genomic DNA of C. acetobutylicum ATCC 824, using the primers Ca_CtfAB for and Ca_CtfAB rev (Table 3). The PCR product is digested with the restriction enzymes xhoI and speI. The digested vector pFC002 and the digested DNA fragment containing the gene Ca_CtfAB are ligated together. The vector thus obtained is designated pFC006 (FIG. 1). The vector is maintained and multiplied in the E. coli strain XL1 blue.

Step 3: Construction of the Vector pFC007 from the Plasmid pFC006

The vector pFC006 is digested with the restriction enzymes xhoI and XbaI. The gene coding for Ca_Adc is amplified from the genomic DNA of C. acetobutylicum ATCC 824, using the primers Ca_adc for and Ca_adc rev (Table 3). The PCR product is digested with the enzymes xhoI and SpeI. The digested vector pFC006 and the digested DNA fragment containing the gene Ca_adc are ligated together. The vector thus obtained is designated pFC007 (FIGS. 1 and 3). The vector is maintained and multiplied in the E. coli strain XL1 blue.

TABLE 3

Primers used for constructing the ipa operons

| Primers | Sequence (5'-3') |
|---|---|
| Ca_thlp-for | GCATGCGAATTTAGAATGAAGTTTCTTATGCA (SEQ ID NO: 7) |
| Ca_thlp_rev | GGGCCCCCATAGTTTATCCCTAATTTATACG (SEQ ID NO: 8) |
| Cb_s-adh-for | GGGCCCTTAGACTATTAAAGGAATATTTTTAAGG (SEQ ID NO: 9) |
| Cb_s-adh-rev | TTTTCTCGAGGTATAATCCTCCATGATCTATTATG (SEQ ID NO: 10) |
| Ca_ctf A &B for | CAACTACTCGAGATAATTTTTTCTAGAGAATTTAAAAGGAGGGATTAAAATG (SEQ ID NO: 11) |
| Ca_ctf A &B rev | AATGGTACTAGTTATTTTTTGTCGACTGTTTCATA GTATTTCTTTCTAAACAGCC (SEQ ID NO: 12) |
| Ca_adc for | AAACAACTCGAGTTATAATCTAGATATAAATAAATAGGACTAGAGGCG (SEQ ID NO: 13) |
| Ca_adc rev | AAAAATACTAGTTACCATTTAAGTCGACTCTTATTTTTATTACTTAAG (SEQ ID NO: 14) |

The added restriction sites (sphI, apaI, xhoI, SalI, xbaI and speI) are underlined. The ribosome binding sites are shown in bold.

The prefix "Ca" means that the primer is used on the genomic DNA of C. acetobutylicum The prefix "Cb" means that the primer is used on the genomic DNA of C. beijerinckii NRRL B 593

Using similar methods, the gene coding for Ca_Adc can be inserted into the vector pFC002 to obtain the vector pFC005.

According to similar methods, the genes coding for Ca_CtfAB can then be inserted into the vector pFC005 to obtain the vector pFC008.

Transformation of C. Acetobutylicum

The vectors pFC002, pFC006 and pFC007 are first methylated respectively by cotransformation with the plasmid pAN1 in the E. coli strain DH10B.

The wild-type strain of C. acetobutylicum ATCC 824 is then transformed respectively by the methylated vectors pFC002, pFC006 and pFC007 according to the protocol described by Oultram (1988). The strains of C. acetobutylicum ATCC 824 transformed by pFC002, pFC006 and pFC007 are called ATCC 824(pFC002), ATCC 824(pFC006) and ATCC 824(pFC007), respectively.

Genetic Characterization of the Recombinant Strains

In order to confirm the presence of one of the vectors described above in the strain C. acetobutylicum ATCC 824 after transformation, a PCR specific to the plasmid is carried out with a different primer pair. The results shown in Table 4 confirm the presence of vectors in the recombinant strains analyzed.

TABLE 4

Identification of the vectors pFC005, pFC006 or pFC007 in C. acetobutylicum ATCC 824 by PCR

| | Size of PCR fragments expected [kbp] for the primer pairs: | | | | |
|---|---|---|---|---|---|
| PCR mix | Cb_thl$_p$ for Cb_s-adh rev | Cb_s-adh for Ca_adc rev | Cb_s-adh for Ca_ctfAB rev | Ca_adc for Ca_ctfAB rev | Ca_ctfAB for Ca_adc rev |
| pFC002 | 1.4 | | | | |
| pFC005 | 1.4 | 2.0 | No | No | No |
| pFC006 | 1.4 | No | 2.5 | No | No |
| pFC007 | 1.4 | 2.0 | 3.4 | 2.3 | No |
| pFC008 | 1.4 | 3.4 | 2.5 | No | 2.3 |

Fermentation of the Recombinant Strains

Fermentations were carried out in a culture medium described by Gapes et al. (GAPES et al., 1996), containing 90 g/L of glucose with wild-type strains, C. beijerinckii NRRL B 593 and C. acetobutylicum ATCC 824, and the recombinant strains namely C. acetobutylicum ATCC 824 transformed respectively by the vectors pFC006 and pFC007. The fermentation results are presented in Table 5.

TABLE 5

Final performances on glucose by wild-type and recombinant strains of C. beijerinckii NRRL B 593 and of C. acetobutylicum ATCC 824

| Characteristic | NRRL B 593 wild-type | ATCC 824 wild-type | ATCC 824 (pFC002) | ATCC 824 (pFC006) | ATCC 824 (pFC007) |
|---|---|---|---|---|---|
| Glucose consumed [g/L] | 34.30 | 61.99 | 54.82 | 69.26 | 67.79 |
| Lactic acid [g/L] | 0.55 | 0.00 | −0.16 | 0.17 | 0.19 |
| Acetic acid [g/L] | 0.83 | 2.86 | 4.61 | 3.24 | 1.61 |
| Acetoin [g/L] | 0.00 | 0.59 | 0.10 | 0.06 | 0.05 |
| 2,3-Butanediol [g/L] | 0.00 | 0.08 | 0.48 | 0.91 | 0.88 |
| Butyric acid [g/L] | 0.21 | 2.02 | 2.51 | 1.08 | 1.06 |
| Acetone [g/L] | 0.17 | 5.70 | 0.05 | 0.35 | 0.09 |
| Ethanol [g/L] | 0.12 | 1.26 | 0.31 | 1.34 | 1.71 |
| Isopropanol [g/L] | 4.47 | 0.10 | 4.25 | 7.27 | 8.37 |
| Butanol [g/L] | 8.08 | 8.98 | 8.22 | 11.80 | 12.95 |
| IBE or ABE [g/L] | 12.83 | 16.04 | 12.82 | 20.76 | 23.12 |
| Fermentation time [h]* | 33.5 | 49.5 | >45 | 29.9 | 28.0 |
| Maximum productivity for IBE or ABE [g/L · h] | 0.41 | 0.41 | 0.33 | 0.69 | 0.81 |
| Yield of IBE or ABE [g/g substrate] | 0.37 | 0.26 | 0.24 | 0.30 | 0.34 |
| Selectivity for isopropanol [g/g solvents] | 0.35 | 0.01 | 0.33 | 0.35 | 0.36 |
| Selectivity for acetone [g/g solvents] | 0.01 | 0.36 | <0.01 | 0.02 | 0.00 |

*time necessary to reach 95% of the final production of solvent.

Fermentation of Glucose by the Wild-type Strain *C. Acetobutylicum* ATCC 824

Approximately 50 hours of fermentation are needed to reach 95% of the final production of solvents. The presence of solvent (butanol) can only be detected 11 hours after inoculation. Neither isopropanol nor 2,3-butanediol is produced by the wild-type strain *C. acetobutylicum* ATCC 824. The production of acetone and that of acetoin reach 5.7 g/L and 0.6 g/L respectively. The final productions of butanol and of ethanol reach 9.0 g/L and 1.3 g/L respectively.

Fermentation of Glucose by the Recombinant Strain *C. Acetobutylicum* ATCC 824(pFC002)

*C. acetobutylicum* ATCC 824(pFC002) is a recombinant strain that has received the vector pFC002. The vector pFC002 allows its host constitutive expression of the gene of the secondary alcohol dehydrogenase of *C. beijerinckii* NRRL B 593 (Cb_s-adh) coding for the enzyme Cb_s-Adh. The production of Cb_s-Adh in the recombinant strain ATCC 824(pFC002) makes it possible to hydrogenate acetone and acetoin to isopropanol and 2,3-butanediol respectively. Acetoin is produced naturally by the wild-type strain of *C. acetobutylicum* ATCC 824. However, this recombinant strain is not capable of producing more isopropanol than the wild-type strain of *C. beijerinckii* NRRL B593. Moreover, the strain ATCC 824(pFC002) displays mediocre fermentation performances, thus, the production of isopropanol, and of solvents in general, of the strain ATCC 824(pFC002) is 25% lower than the production of acetone and 20% lower than the production of solvents of the wild-type strain of *C. acetobutylicum* ATCC 824. Acetate and butyrate remain the majority products at the end of the fermentation. The significant production of acids causes the drop in yield of solvents, as a proportion of the carbohydrates is used for the production of acids.

Fermentation of Glucose by the Recombinant Strain *C. Acetobutylicum* ATCC 824(pFC006)

Like the recombinant strain ATCC 824(pFC002), the recombinant strain ATCC 824(pFC006) produces isopropanol and 2,3-butanediol instead of acetone and acetoin.

However, in contrast to the profile of production for the recombinant strain ATCC 824(pFC002), the recombinant strain ATCC 824(pFC006) can reach a high level of production of solvents over a shorter period of time. The time necessary to reach 95% of the final production of solvent for this strain is approximately 30 hours. The consumption of butyric acid is more effective than that of the wild-type strain or of the recombinant strain ATCC 824(pFC002), but remains incomplete. The production of solvents in this strain begins earlier than for the wild-type strain or for the recombinant strain ATCC 824(pFC002). The production of isopropanol can be detected as from the first 10 hours of culture of the strain ATCC 824(pFC006), whereas traces of solvents are not yet detectable in the wild-type strain or in the strain ATCC 824 (pFC002).

Moreover, the incorporation of acetate and of butyrate in the strain ATCC 824(pFC006) are both improved relative to those in the wild-type strain, which makes it possible to have an isopropanol yield better than the acetone yield of the wild-type strain. For the strain ATCC 824(pFC007), the respective titres of isopropanol, butanol and ethanol are 7.3 g/L, 11.8 g/L and 1.37 g/L, in other words 28%, 31% and 6% higher than those of the wild-type strain. The productivity is increased from 0.41 g/L·h for a wild-type strain to 0.69 g/L·h for the strain ATCC 824(pFC007).

The strain ATCC 824(pFC006) produces twice as much 2,3-butanediol than the strain ATCC 824(pFC002), and this increase in production of 2,3-butanediol may be due to an overall improvement in metabolic flux.

It is found that the improvement in the incorporation of acids allows the strain ATCC 824(pFC006) to produce less acids and to increase its production of solvents.

However, despite overexpression of the enzyme Ca_Ct-fAB, the final production of acetate is higher in the strain ATCC 824(pFC006) than in the wild-type strain, which may be due to increased production of acids as a result of an overall improvement in metabolic flux.

Fermentation of Glucose by the Recombinant Strain *C. Acetobutylicum* ATCC 824 Transformed by pFC007

The strain ATCC 824(pFC007) has a fermentation profile similar to that of the strain ATCC 824(pFC006). The time to reach 95% of the final production of solvents is less than 30 hours. Acidogenesis begins normally. The production of solvents in the strain ATCC 824(pFC007) begins during the exponential phase and earlier than in the wild-type strain. The presence of isopropanol can be detected in the culture medium of the strain ATCC 824(pFC007), only 4 hours after inoculation, whereas acetone is not yet detectable in the culture medium of a wild-type strain.

Moreover, the incorporation of acetate and of butyrate in the strain ATCC 824(pFC007) are both improved relative to those in the strain ATCC 824(pFC006), which makes it possible to have a better isopropanol yield relative to that of the strain ATCC 824(pFC006), or of other strains described previously. In the strain ATCC 824(pFC007), the respective titres of isopropanol, butanol and ethanol are 8.4 g/L, 13.0 g/L and 1.71 g/L, in other words 46%, 44% and 36% higher than those of the wild-type strain. Productivity is increased from 0.41 g/L·h for a wild-type strain to 0.81 g/L·h for the strain ATCC 824(pFC007).

The production of 2,3-butanediol, of the strain ATCC 824 (pFC007), is similar to that of the strain ATCC 824(pFC006). As for the strain ATCC 824(pFC006), this increase in the production of 2,3-butanediol may be due to an overall improvement in metabolic flux.

Fermentation of Glucose by the Wild-type Strain *C. Beijerinckii* NRRL B 593

The wild-type strain *C. beijerinckii* NRRL B 593 is cultivated under the same conditions as the wild-type or recombinant strain *C. acetobutylicum* ATCC 824.

After 34 hours of fermentation, the wild-type strain of *C. beijerinckii* reaches 95% of the final production of solvents. However, the final productions of this strain are only 4.5 g/L for isopropanol, 8.1 g/L for butanol and 0.1 g/L for ethanol, which is lower than for the wild-type strain *C. acetobutylicum* ATCC 824 and for the recombinant strains *C. acetobutylicum* ATCC 824 (strains ATCC 824(pFC006) and ATCC 824 (pFC007).

As expected, the wild-type strain *C. beijerinckii* NRRL B 593 does not produce acetoin or butanediol.

CONCLUSION

The recombinant strains ATCC 824(pFC006) and ATCC 824(pFC007) both exhibit better solvents productivity than the wild-type strain *C. acetobutylicum* ATCC 824 or than the wild-type strain *C. beijerinckii* NRRL B 593. The solvents productivity is multiplied respectively by a factor of 1.8 with the strain ATCC 824(pFC006) and by a factor of 2 with the strain ATCC 824(pFC007). These results show that these two strains can produce more solvents for a shorter time than the wild-type strains. Moreover, the strain ATCC 824(pFC007) has been found to be very suitable for continuous single-stage culture (a single fermenter). The productions of isopropanol, butanol and ethanol observed were to those known for the strain *C. beijerinckii* NRRL B 593 (Shrikant A., 2011) and *C. acetobutylicum* ATCC824(pFC007) (Godin et al 1990)

REFERENCES

Chen J S (1995) Alcohol-Dehydrogenase—Multiplicity and Relatedness in the Solvent-Producing Clostridia. FEMS Microbiol Rev 17:263-273

Chen J-S, Hiu S F (1986) Acetone-butanol-isopropanol production by *Clostridium beijerinckii* (synonym, *Clostridium butylicum*). Biotechnol Lett 8:371-376

Gapes J R, Nimcevic D, Friedl A (1996) Long-Term Continuous Cultivation of *Clostridium beijerinckii* in a Two-Stage Chemostat with On-Line Solvent Removal. Appl Environ Microbiol 62:3210-3219

George H A, Johnson J L, Moore W E C, Holdeman L V, Chen J S (1983) Acetone, Isopropanol, and Butanol Production by *Clostridium beijerinckii* (syn. *Clostridium butylicum*) and *Clostridium aurantibutyricum*. Appl. Environ. Microbiol. 45:1160-1163

Goihberg, E., et al., Biochemical and Structural Properties of Chimeras Constructed by Exchange of Cofactor-Binding Domains in Alcohol Dehydrogenases from Thermophilic and Mesophilic Microorganisms. Biochemistry, 2010. 49(9): p. 1943-1953

Hanai T, Atsumi S, Liao J C (2007) Engineered synthetic pathway for isopropanol production in *Escherichia coli*. Appl Environ Microbiol 73:7814-7818

Heap J T, Pennington O J, Cartman S T, Carter G P, Minton N P (2007) The ClosTron: A universal gene knock-out system for the genus *Clostridium*. J Microbiol Methods 70:452-464

Ismaiel A A, Zhu C X, Colby G D, Chen J S (1993) Purification and characterization of a primary-secondary alcohol dehydrogenase from two strains of *Clostridium beijerinckii*. J Bacteriol 175:5097-5105

Johnson J L, Toth J, Santiwatanakul S, Chen J S (1997) Cultures of "*Clostridium acetobutylicum*" from various collections comprise *Clostridium acetobutylicum*, *Clostridium beijerinckii*, and two other distinct types based on DNA-DNA reassociation. International Journal of Systematic Bacteriology 47:420-424

Jojima T, Inui M, Yukawa H (2008) Production of isopropanol by metabolically engineered *Escherichia coli*. Applied Microbiol Biotechnol 77:1219-1224

Jones, D. T. and D. R. Woods, Acetone butanol fermentation revisited Microbiological Reviews, 1986. 50(4): p. 484-524

Keis S, Shaheen R, Jones D T (2001) Emended descriptions of *Clostridium acetobutylicum* and *Clostridium beijerinckii*, and descriptions of *Clostridium saccharoperbutylacetonicum* sp. nov. and *Clostridium saccharobutylicum* sp. nov. Int J Syst Evol Microbiol 51:2095-2103

Korkhin Y, Kalb A J, Peretz M, Bogin O, Burstein Y, Frolow E (1999) Oligomeric integrity—The structural key to thermal stability in bacterial alcohol dehydrogenases. Protein Science 8:1241-1249

Korkhin Y, Kalb A J, Peretz M, Bogin O, Burstein Y, Frolow F (1998) NADP-dependent bacterial alcohol dehydrogenases: Crystal structure, cofactor-binding and cofactor specificity of the ADHs of *Clostridium beijerinckii* and *Thermoanaerobacter brockii*. J Molecular Biol 278:967-981

Langlykke A F, Peterson W H, Fred E B (1937) Reductive Processes of *Clostridium butylicum* and the Mechanism of Formation of Isopropyl Alcohol. J Bacteriol 34:443-453

Logsdon J E, Loke R A (2001) Isopropyl alcohol. In: Kirk-Othmer Encyclopedia of Chemical Technology. John Wiley & Sons, Inc.

Mermelstein, L. D., et al., Metabolic engineering of *Clostridium acetobutylicum* ATCC 824 for increased solvent production by enhancement of acetone formation enzyme activities using a synthetic acetone operon. Biotechnology and Bioengineering, 1993. 42(9): p. 1053-1060

Mermelstein, L. D. and E. T. Papoutsakis, Invivo Methylation in *Escherichia-Coli* by the *Bacillus-Subtilis* Phage-Phi-3t-I Methyltransferase to Protect Plasmids from Restriction Upon Transformation of *Clostridium-Acetobutylicum* Atcc-824. Applied and Environmental Microbiology, 1993. 59(4): p. 1077-1081

Mujiburohman M, Sediawan W B, Sulistyo H (2006) A preliminary study: Distillation of isopropanol-water mixture using fixed adsorptive distillation method. Separation and Purification Technology 48:85-92

Nolling, J., et al., Genome sequence and comparative analysis of the solvent-producing bacterium *Clostridium acetobutylicum*. Journal of Bacteriology, 2001. 183(16): p. 4823-4838

Osburn O L, Brown R W, Werkman C H (1937) The butyl alcohol-isopropyl alcohol fermentation. J Biol Chem 121: 685-695

Oultram J D, Peck H, Brehm J K, Thompson D E, Swinfield T J, Minton N P (1988) Introduction of Genes for Leucine Biosynthesis from *Clostridium-Pasteurianum* into *Clostridium-Acetobutylicum* by Cointegrate Conjugal Transfer. Mol Gen Genetics 214:177-179

Papa A (2005) Propanols. In: Ullmann's Encyclopedia of Industrial Chemistry. Wiley-VCH Verlag GmbH & Co. KGa, Weinheim Petersen, D. J. and G. N. Bennett, Purification of acetoacetate decarboxylase from *Clostridium acetobutylicum* ATCC 824 and cloning of the acetoacetate decarboxylase gene in *Escherichia coli*. Appl Environ Microbiol, 1990. 56(11): p. 3491-8

Peretz M et al. (1997) Molecular cloning, nucleotide sequencing, and expression of genes encoding alcohol dehydrogenases from the thermophile *Thermoanaerobacter brockii* and the mesophile *Clostridium beijerinckii*. Anaerobe 3:259-270

Rogers P, Chen J-S, Zidwick M (2006) Organic acid and solvent production. Part III; butanol, acetone, isopropanol; 1,3- and 1,2-propanediol production; and 2,3-butanediol production. In: Dworkin M (ed) The prokaryotes. A handbook on the biology of bacteria. 3rd edition. Springer, N.Y., USA, pp 672-755

Survase S A, Jurgens G, van Heiningen A, Granström T. (2011) Continuous production of isopropanol and butanol using *Clostridium beijerinckii* DSM 6423. Appl Microbiol Biotechnol. September; 91(5):1305-13.

Wiesenborn D P, Rudolph F B, Papoutsakis E T (1988) Thiolase from *Clostridium acetobutylicum* ATCC 824 and Its Role in the Synthesis of Acids and Solvents. Appl Environ Microbiol 54:2717-2722

Yan R T, Zhu C X, Golemboski C, Chen J S (1988) Expression of Solvent-Forming Enzymes and Onset of Solvent Production in Batch Cultures of *Clostridium beijerinckii* ("*Clostridium butylicum*"). Appl Environ Microbiol 54:642-648

The invention claimed is:

1. A vector comprising:
   a nucleic acid represented by the sequence SEQ ID NO: 1, or a nucleic acid having a sequence identity of at least 85% with the sequence SEQ ID NO: 1, coding for subunit A of the acetoacetyl-CoA transferase of *C. acetobutylicum* and
   a nucleic acid represented by the sequence SEQ ID NO: 2 or a nucleic acid having a sequence identity of at least 85% with the sequence SEQ ID NO: 2, coding for subunit B of the acetoacetyl-CoA transferase of *C. acetobutylicum*, and
   optionally a nucleic acid represented by the sequence SEQ ID NO: 4 or a nucleic acid having a sequence identity of at least 85% with the sequence SEQ ID NO: 4, coding for the acetoacetate decarboxylase of *C. acetobutylicum*, and
   a nucleic acid represented by the sequence SEQ ID NO: 3 or a nucleic acid having a sequence identity of at least 85% with the sequence SEQ ID NO: 3, coding for the secondary alcohol dehydrogenase of *C. beijerinckii*,
   the expression of said nucleic acids being controlled by a single constitutive promoter located upstream of the abovementioned nucleic acids, said promoter being selected from the promoter represented by the sequence SEQ ID NO: 5(thl promoter) and the promoter represented by the sequence SEQ ID NO: 6.

2. The expression vector according to claim 1, wherein said vector comprises:
   a nucleic acid represented by the sequence SEQ ID NO: 1,
   a nucleic acid represented by the sequence SEQ ID NO: 2,
   a nucleic acid represented by the sequence SEQ ID NO: 3,
   a nucleic acid represented by the sequence SEQ ID NO: 4, and
   a promoter represented by the sequence SEQ ID NO: 5.

3. The expression vector according to claim 1, wherein said vector comprises:
   a nucleic acid represented by the sequence SEQ ID NO: 1,
   a nucleic acid represented by the sequence SEQ ID NO: 2,
   a nucleic acid represented by the sequence SEQ ID NO: 3, and
   a promoter represented by the sequence SEQ ID NO: 5.

4. A microorganism comprising the expression vector according to claim 1.

5. The microorganism according to claim 4, wherein said microorganism is a bacteria of the genera selected from the group consisting of *Clostridium*, *Bacillus*, and enterobacteria.

6. The microorganism according to claim 5, wherein said microorganism is selected from the group consisting of *Clostridium acetobutylicum*, *Clostridium beijerinckii*, *Clostridium saccharoperbutylacetonicum*, and *Clostridium saccharobutylicum*.

7. The microorganism according to claim 5, wherein said microorganism is *E. coli*.

8. A method for the production of isopropanol, and/or of D and L 2,3-butanediol, said method comprising:
   cultivating a microorganism according to claim 4, in a culture medium comprising at least one carbon source and one nitrogen source, under conditions allowing the production of isopropanol, and
   recovering the isopropanol, and/or D and L 2,3-butanediol, from the culture medium.

9. The expression vector according to claim 1, wherein the expression vector does comprise the nucleic acid represented by the sequence SEQ ID NO: 4 or a nucleic acid having a sequence identity of at least 85% with the sequence SEQ ID NO: 4, coding for the acetoacetate decarboxylase of *C. acetobutylicum*.

10. The expression vector according to claim 1, wherein the expression vector does not comprise the nucleic acid represented by the sequence SEQ ID NO: 4 or a nucleic acid having a sequence identity of at least 85% with the sequence SEQ ID NO: 4, coding for the acetoacetate decarboxylase of *C. acetobutylicum*.

\* \* \* \* \*

SEQUENCE LISTING

<160> NUMBER OF SEQ ID NOS: 14

<210> SEQ ID NO 1
<211> LENGTH: 646
<212> TYPE: DNA
<213> ORGANISM: Clostridium acetobutylicum

<400> SEQUENCE: 1

```
atgaactcta aaataattag atttgaaaat ttaaggtcat tctttaaaga tgggatgaca      60
attatgattg gaggtttttt aaactgtggc actccaacca aattaattga ttttttagtt     120
aatttaaata taaagaattt aacgattata agtaatgata catgttatcc taatacaggt     180
attggtaagt taatatcaaa taatcaagta aaaaagctta ttgcttcata tataggcagc     240
aacccagata ctggcaaaaa actttttaat aatgaacttg aagtagagct ctctccccaa     300
ggaactctag tggaaagaat acgtgcaggc ggatctggct taggtggtgt actaactaaa     360
acaggtttag gaactttgat tgaaaaagga aagaaaaaaa tatctataaa tggaacggaa     420
tatttgttag agctacctct tacagccgat gtagcattaa ttaaaggtag tattgtagat     480
gaggccggaa acaccttcta taaaggtact actaaaaact ttaatcccta tatggcaatg     540
gcagctaaaa ccgtaatagt tgaagctgaa aatttagtta gctgtgaaaa actagaaaag     600
gaaaaagcaa tgacccccgg agttcttata aattatatag taaagg                    646
```

<210> SEQ ID NO 2
<211> LENGTH: 655
<212> TYPE: DNA
<213> ORGANISM: Clostridium acetobutylicum

<400> SEQUENCE: 2

```
gcctgcataa aatgattaat gataaaaacc tagcgaaaga aataatagcc aaaagagttg      60
caagagaatt aaaaaatggt caacttgtaa acttaggtgt aggtcttcct accatggttg     120
cagattatat accaaaaaat ttcaaaatta ctttccaatc agaaaacgga atagttggaa     180
tgggcgctag tcctaaaata aatgaggcag ataaagatgt agtaaatgca ggaggagact     240
atacaacagt acttcctgac ggcacatttt tcgatagctc agtttcgttt tcactaatcc     300
gtggtggtca cgtagatgtt actgttttag ggggctctcca ggtagatgaa aagggtaata     360
tagccaattg gattgttcct ggaaaaatgc tctctggtat gggtggagct atggatttag     420
taaatggagc taagaaagta ataattgcaa tgagacatac aaataaaggt caacctaaaa     480
ttttaaaaaa atgtacactt cccctcacgg caaagtctca agcaaatcta attgtaacag     540
aacttggagt aattgaggtt attaatgatg gtttacttct cactgaaatt aataaaaaca     600
caaccattga tgaaataagg tctttaactg ctgcagattt actcatatcc aatga          655
```

<210> SEQ ID NO 3
<211> LENGTH: 1121
<212> TYPE: DNA
<213> ORGANISM: Clostridium beijerinckii

<400> SEQUENCE: 3

```
ttagactatt aaaggaatat ttttaaggag gaacatattt tatgaaaggt tttgcaatgc      60
taggtattaa taagttagga tggatcgaaa aagaaaggcc agttgcgggt tcatatgatg     120
ctattgtacg cccattagca gtatctccgt gtacatcaga tatacatact gtttttgagg     180
gagctcttgg agataggaag aatatgattt tagggcatga agctgtaggt gaagttgttg     240
aagtaggaag tgaagtgaag gattttaaac ctggtgacag agttatagtt ccttgtacaa     300
```

```
ctccagattg gagatctttg gaagttcaag ctggttttca acagcactca aacggtatgc    360
tcgcaggatg gaaattttca aatttcaagg atggagtttt tggtgaatat tttcatgtaa    420
atgatgcgga tatgaatctt gcgattctac ctaaagacat gccattagaa aatgctgtta    480
tgataacaga tatgatgact actggatttc atggagcaga acttgcagat attcaaatgg    540
gttcaagtgt tgtggtaatt ggcattggag ctgttggctt aatgggaata gcaggtgcta    600
attacgtgga gcaggtagaa taattggagt ggggagcagg ccgatttgtg ttgaggctgc    660
aaaattttat ggagcaacag atattctaaa ttataaaaat ggtcatatag ttgatcaagt    720
tatgaaatta cgaatggaa aaggcgttga ccgcgtaatt atggcaggcg gtggttctga    780
aacattatcc caagcagtat ctatggttaa accaggagga ataatttcta atataaatta    840
tcatggaagt ggagatgctt tactaatacc acgtgtagaa tggggatgtg aatggctca    900 caagactata aaggaggtc tttgtcctgg gggacgtttg agagcagaaa tgttaagaga    960
tatggtagta tataatcgtg ttgatctaag taaattagtt acacatgtat atcatggatt   1020
tgatcacata gaagaagcac tgttattaat gaaagacaag ccaaaagact aattaaagc    1080 agtagttata ttataacata atagatcatg gaggattata c                       1121

<210> SEQ ID NO 4
<211> LENGTH: 865
<212> TYPE: DNA
<213> ORGANISM: Clostridium acetobutylicum

<400> SEQUENCE: 4
aaacaattat aatataaata aataggacta gaggcgattt ataatgtgaa gataaagtat     60
gttagaaaag ctaaacatta ttaaatttag gaaggtgact tttatgttaa aggatgaagt    120
aattaaacaa attagcacgc cattaacttc gcctgcattt cctagaggac cctataaatt    180
tcataatcgt gagtatttta acattgtata tcgtacagat atggatgcac ttcgtaaagt    240
tgtgccagag cctttagaaa ttgatgagcc cttagtcagg tttgaaatta tggcaatgca    300
tgatacgagt ggacttggtt gttatacaga aagcggacag gctattcccg taagctttaa    360
tggagttaag ggagattatc ttcatatgat gtatttagat aatgagcctg caattgcagt    420
aggaagggaa ttaagtgcat atcctaaaaa gctcgggtat ccaaagcttt ttgtggattc    480
agatacttta gtaggaactt tagactatgg aaaacttaga gttgcgacag ctacaatggg    540
gtacaaacat aaagccttag atgctaatga agcaaaggat caaatttgtc gccctaatta    600
tatgttgaaa ataatacccca attatgatgg aagccctaga atatgtgagc ttataaatgc    660
gaaaatcaca gatgttaccg tacatgaagc ttggacagga ccaactcgac tgcagttatt    720
tgatcacgct atggcgccac ttaatgattt gccagtaaaa gagattgttt ctagctctca    780
cattcttgca gatataatat tgcctagagc tgaagttata tatgattatc ttaagtaata    840
aaaataagat aaatggtaa ttttt                                           865

<210> SEQ ID NO 5
<211> LENGTH: 242
<212> TYPE: DNA
<213> ORGANISM: Clostridium acetobutylicum

<400> SEQUENCE: 5
gaatttagaa tgaagtttct tatgcacaag tatttttat tacattaata tagttaaaat     60
ataaacttat gtatttatgc taaaacatga ttttaagggg gttagcatat gcataagttt    120
```

```
aatttttttg ttaaaaaata ttaaactttg tgttttttt  aacaaaatat attgataaaa      180
ataataatag tgggtataat taagttgtta gagaaaacgt ataaattagg gataaactat      240
gg                                                                    242
```

<210> SEQ ID NO 6
<211> LENGTH: 145
<212> TYPE: DNA
<213> ORGANISM: Clostridium acetobutylicum

<400> SEQUENCE: 6

```
cgactgtgga tggagttaag tcagcagaaa gtataatgag aaaatataaa atataaataa       60
ttttctaaaa aacttaactt catgtgaaaa gtttgttaaa atataaatga gcacgttaat      120
catttaacat agataattaa atagt                                           145
```

<210> SEQ ID NO 7
<211> LENGTH: 32
<212> TYPE: DNA
<213> ORGANISM: Artificial Sequence
<220> FEATURE:
<223> OTHER INFORMATION: synthesized primer

<400> SEQUENCE: 7

```
gcatgcgaat ttagaatgaa gtttcttatg ca                                    32
```

<210> SEQ ID NO 8
<211> LENGTH: 31
<212> TYPE: DNA
<213> ORGANISM: Artificial Sequence
<220> FEATURE:
<223> OTHER INFORMATION: synthesized primer

<400> SEQUENCE: 8

```
gggcccccat agtttatccc taatttatac g                                     31
```

<210> SEQ ID NO 9
<211> LENGTH: 34
<212> TYPE: DNA
<213> ORGANISM: Artificial Sequence
<220> FEATURE:
<223> OTHER INFORMATION: synthesized primer

<400> SEQUENCE: 9

```
gggcccttag actattaaag gaatattttt aagg                                  34
```

<210> SEQ ID NO 10
<211> LENGTH: 35
<212> TYPE: DNA
<213> ORGANISM: Artificial Sequence
<220> FEATURE:
<223> OTHER INFORMATION: synthesized primer

<400> SEQUENCE: 10

```
ttttctcgag gtataatcct ccatgatcta ttatg                                 35
```

<210> SEQ ID NO 11
<211> LENGTH: 55
<212> TYPE: DNA
<213> ORGANISM: Artificial Sequence
<220> FEATURE:
<223> OTHER INFORMATION: synthesized primer

<400> SEQUENCE: 11

```
aatggtacta gttattttt gtcgactgtt tcatagtatt tctttctaaa cagcc            55
```

```
<210> SEQ ID NO 12
<211> LENGTH: 55
<212> TYPE: DNA
<213> ORGANISM: Artificial Sequence
<220> FEATURE:
<223> OTHER INFORMATION: synthesized primer

<400> SEQUENCE: 12
aatggtacta gttattttt gtcgactgtt tcatagtatt tctttctaaa cagcc            55

<210> SEQ ID NO 13
<211> LENGTH: 48
<212> TYPE: DNA
<213> ORGANISM: Artificial Sequence
<220> FEATURE:
<223> OTHER INFORMATION: synthesized primer

<400> SEQUENCE: 13
aaacaactcg agttataatc tagatataaa taaataggac tagaggcg                   48

<210> SEQ ID NO 14
<211> LENGTH: 48
<212> TYPE: DNA
<213> ORGANISM: Artificial Sequence
<220> FEATURE:
<223> OTHER INFORMATION: synthesized primer

<400> SEQUENCE: 14
aaaaatacta gttaccattt aagtcgactc ttatttttat tacttaag                   48
```